(12) United States Patent
Nahman et al.

(10) Patent No.: US 10,157,626 B2
(45) Date of Patent: Dec. 18, 2018

(54) VOICE AFFECT MODIFICATION

(71) Applicant: Harman International Industries, Inc., Stamford, CT (US)

(72) Inventors: Jaime Elliot Nahman, Oakland, CA (US); Stefan Marti, Oakland, CA (US); Davide Di Censo, Oakland, CA (US)

(73) Assignee: HARMAN INTERNATIONAL INDUSTRIES, INCORPORATED, Stamford, CT (US)

(*) Notice: Subject to any disclaimer, the term of this patent is extended or adjusted under 35 U.S.C. 154(b) by 0 days.

(21) Appl. No.: 15/002,320

(22) Filed: Jan. 20, 2016

(65) Prior Publication Data

US 2017/0206913 A1 Jul. 20, 2017

(51) Int. Cl.
*G10L 21/00* (2013.01)
*G10L 25/00* (2013.01)
*G10L 21/007* (2013.01)
*G10L 25/63* (2013.01)
*G06F 3/0484* (2013.01)
*G06F 3/01* (2006.01)
*A61B 5/04* (2006.01)
*A61B 5/0476* (2006.01)
*A61B 5/16* (2006.01)
*A61B 5/00* (2006.01)
*G10L 13/033* (2013.01)

(52) U.S. Cl.
CPC .......... *G10L 21/007* (2013.01); *A61B 5/0075* (2013.01); *A61B 5/04012* (2013.01); *A61B 5/0476* (2013.01); *A61B 5/165* (2013.01); *G06F 3/017* (2013.01); *G06F 3/04842* (2013.01); *G10L 13/033* (2013.01); *G10L 25/63* (2013.01)

(58) Field of Classification Search
None
See application file for complete search history.

(56) References Cited

U.S. PATENT DOCUMENTS

| 9,431,003 B1* | 8/2016 | Cecchi | G10L 13/033 |
| 2008/0147413 A1 | 6/2008 | Sobol-Shikler | |
| 2012/0016674 A1 | 1/2012 | Basson et al. | |
| 2013/0063256 A1* | 3/2013 | Tartz | G06F 3/005 340/407.1 |
| 2013/0085808 A1* | 4/2013 | Forbes | G06Q 30/0203 705/7.32 |
| 2013/0121591 A1* | 5/2013 | Hill | G06K 9/46 382/195 |
| 2014/0089399 A1 | 3/2014 | Chun et al. | |

(Continued)

OTHER PUBLICATIONS

"Affect display", Wikipedia, 6 pages, https://en.wikipedia.org/wiki/Affect_display.

(Continued)

*Primary Examiner* — Kevin Ky
(74) *Attorney, Agent, or Firm* — Artegis Law Group, LLP

(57) ABSTRACT

A technique for modifying an affect of a voice. The technique includes determining an emotional state associated with a person, and modifying one or more acoustic characteristics of a voice sample acquired from the person based on the emotional state to alter an affect associated with the voice sample. The technique further includes generating a second voice sample based on the one or more acoustic characteristics that have been modified, and transmitting the second voice sample.

19 Claims, 4 Drawing Sheets

(56) References Cited

U.S. PATENT DOCUMENTS

| | | | |
|---|---|---|---|
| 2014/0112556 A1 | 4/2014 | Kalinli-Akbacak | |
| 2014/0169795 A1* | 6/2014 | Clough | G06F 19/3418 |
| | | | 398/106 |
| 2014/0223462 A1* | 8/2014 | Aimone | H04N 21/42201 |
| | | | 725/10 |
| 2015/0154775 A1* | 6/2015 | Tobita | G06F 17/30247 |
| | | | 345/619 |
| 2016/0191958 A1* | 6/2016 | Nauseef | H04N 21/23418 |
| | | | 725/116 |

OTHER PUBLICATIONS

"Speech motion analysis", Scholarpedia, 6 pages http://www.scholarpedia.org/article/Speech_emotion_analysis.

Extended European Search Report for Application No. EP 17150747.8 dated Jun. 8, 2017.

Szekely et al., "Facial Expression-based Affective Speech Translation", Journal of Multimodal User Interfaces, vol. 8, No. 1, Jul. 30, 2013, pp. 87-96, XP055376387, Berlin/Heidelberg.

Gunes et al., "Bi-modal emotion recognition from expressive face and body gestures", Journal of Network and Computer Applications, Academic Press, New York, NY, US, vol. 30, No. 4, Aug. 17, 2007, pp. 1334-1345, XP022206574.

Liu et al., "Real-Time EEG-Based Emotion Recognition and Its Applications", Jan. 1, 2010, Network and Parallel Computing, Springer International Publishing, Cham, pp. 256-277, XP047294677.

Bebe et al., "Multimodal Approaches for Emotion Recognition: A Survey", SPIE—International Society for Optical Engineering Proceedings, vol. 5670, Jan. 17, 2005, XP055376412, 12 pages.

\* cited by examiner

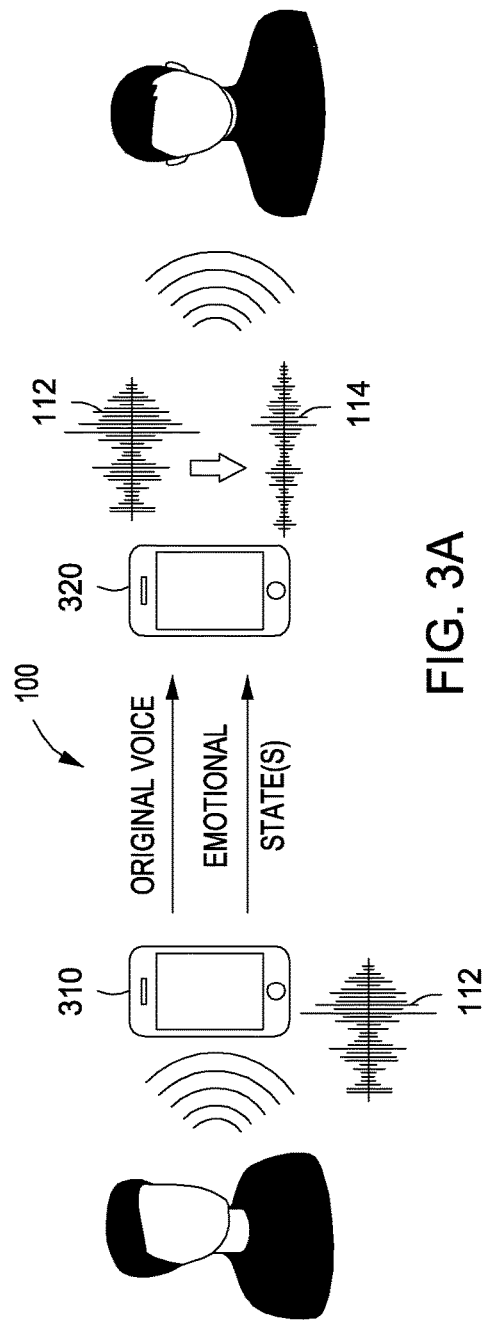
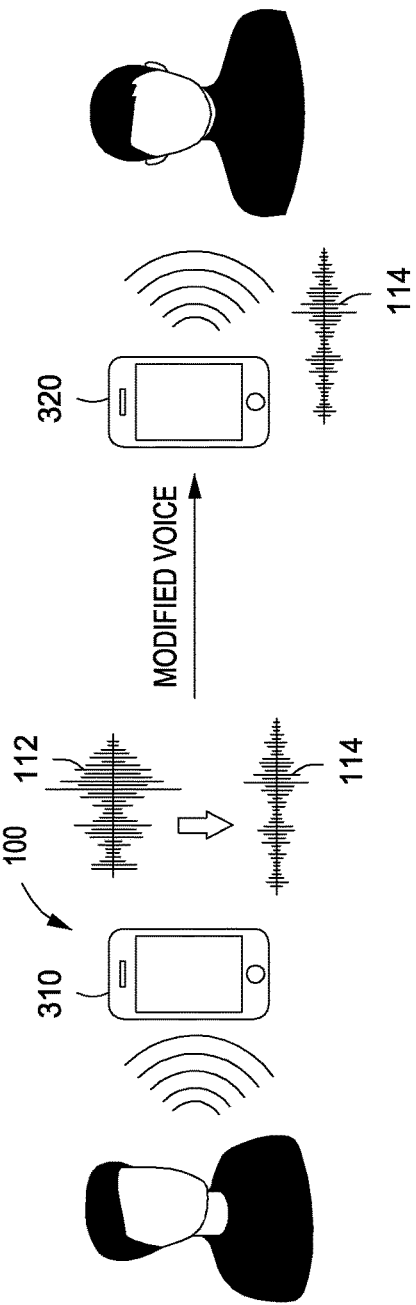

VOICE AFFECT MODIFICATION

BACKGROUND

Field of the Embodiments

The various embodiments relate generally to audio signal processing and, more specifically, to techniques for voice affect modification.

Description of the Related Art

Effective communication plays an important role in developing and maintaining healthy social connections and business relationships. Nevertheless, when involved in conversations, many people have difficulty accurately conveying their emotional state and/or accurately determining the emotional states of those around them or of those directly involved in the conversations. For example, different cultures commonly express emotion via different types of facial expressions, hand gestures, body gestures, etc. Consequently, due to these cultural differences, people from different cultural backgrounds may have difficult effectively conveying their emotions to one another during a conversation. As another example, people with autism spectrum disorders commonly have difficult accurately conveying their emotions and interpreting the emotions of others when communicating or interacting with other people.

In an effort to enable people to more effectively convey their emotional state when communicating, some forms of electronic communication enable users to explicitly indicate their emotions via graphical symbols. For example, many text messaging platforms include graphical facial expressions (i.e., emoticons) that a user can select to graphically convey his or her emotional state to another user. Outside of these types of platforms, however, there currently are no systems available that automatically assist users in conveying and interpreting emotional states during live and/or in-person interactions. Consequently, due to their inability to effectively convey and interpret emotional states, many people continue to struggle with communications and social interactions, which inhibit their ability to develop and maintain healthy relationships.

As the foregoing illustrates, more effective techniques for conveying and interpreting the emotional states of people when communicating or interacting with one another would be useful.

SUMMARY

Embodiments of the present disclosure set forth a method for modifying an affect of a voice. The method includes determining an emotional state associated with a person, and modifying one or more acoustic characteristics of a voice sample acquired from the person based on the emotional state to alter an affect associated with the voice sample. The method further includes generating a second voice sample based on the one or more acoustic characteristics that have been modified, and transmitting the second voice sample.

Further embodiments provide, among other things, a system and a non-transitory computer-readable storage medium configured to implement the techniques set forth above.

At least one advantage of the disclosed techniques is that the affect of the voice of a speaker can be enhanced to enable the speaker to more effectively convey their emotional state and/or to assist a listener in more effectively determining the emotional state of the speaker. In addition, the affect in the voice of a speaker can be reduced and/or changed, for example, and without limitation, to mask an emotional state of the speaker. Moreover, the emotional state of a speaker may be automatically determined via one or more types of sensor data, without requiring interaction from the speaker or listener.

BRIEF DESCRIPTION OF THE SEVERAL VIEWS OF THE DRAWINGS

So that the manner in which the recited features of the one or more embodiments set forth above can be understood in detail, a more particular description of the one or more embodiments, briefly summarized above, may be had by reference to certain specific embodiments, some of which are illustrated in the appended drawings. It is to be noted, however, that the appended drawings illustrate only typical embodiments and are therefore not to be considered limiting of its scope in any manner, for the scope of the various embodiments subsumes other embodiments as well.

FIGS. 3A and 3B illustrate different techniques for generating modified voice samples via the voice affect modification system of FIG. 1, according to various embodiments.

DETAILED DESCRIPTION

In the following description, numerous specific details are set forth to provide a more thorough understanding of the embodiments of the present disclosure. However, it will be apparent to one of skill in the art that the embodiments of the present disclosure may be practiced without one or more of these specific details.

As described above, many people have difficulty accurately conveying their emotional state and/or accurately interpreting the emotional state of a person with whom they are communicating. For example, and without limitation, cultural differences, anxiety, neurological disorders, poor communication skills, etc. could prevent a speaker from effectively utilizing verbal and/or non-verbal cues to convey his or her emotions. Similarly, such issues could prevent a listener from accurately interpreting the emotions conveyed by others.

Accordingly, in order to facilitate more effective communication of emotions between conversants, the voice affect modification system (hereinafter "voice system") may determine an emotional state associated with a user and then modify one or more acoustic characteristics of a voice sample acquired from the user based on the emotional state. More specifically, acoustic characteristics of a voice sample, such as the pitch, vocal quality, timbre, vocal perturbation, voice intonation, loudness, prosody, speech pattern, and/or speech rate of the voice sample, may be modified to enhance, reduce, and/or change the affect of the voice sample. The modified voice sample is then outputted to the person with whom the user is communicating, enabling the intended emotional state(s) of the user to be more effectively conveyed and interpreted. In various embodiments, the voice system makes only subtle changes to the acoustic characteristics of voice samples when modifying affect so that the conversational parties are not distracted by the operation of the voice system.

Figure 1:
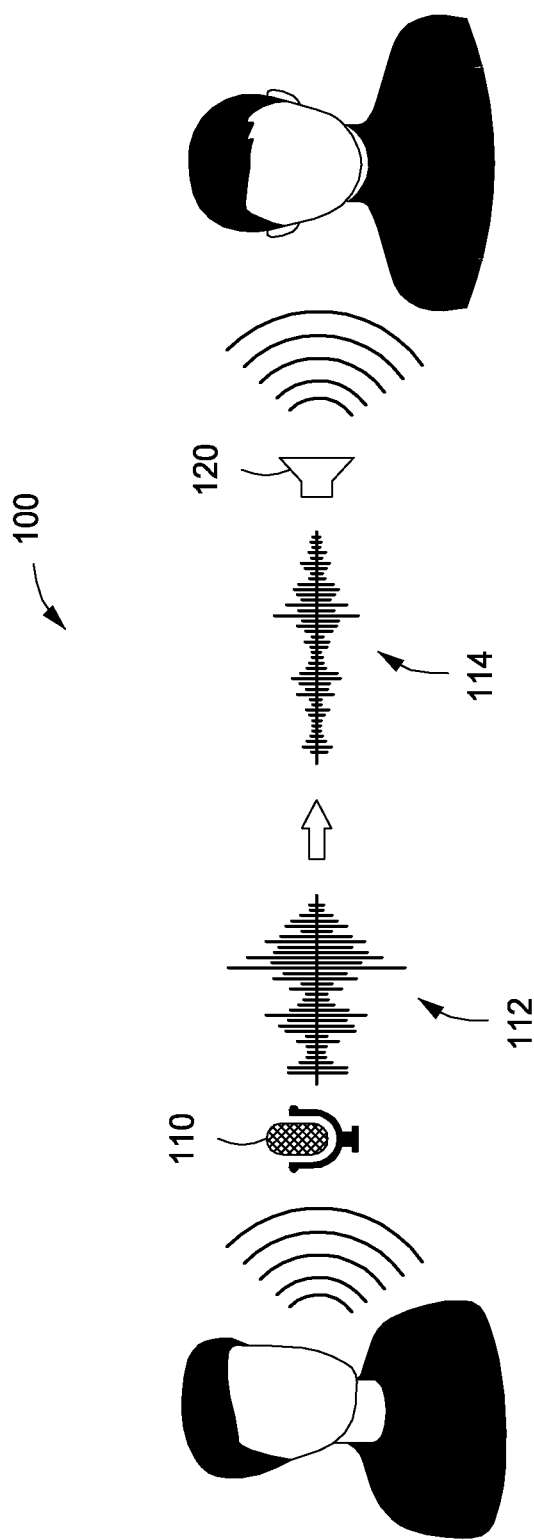
FIG. 1 is a conceptual illustration of how a voice affect modification system can modify the affect of the voice of a user during a conversation, according to various embodiments.

FIG. 1 is a conceptual illustration of how a voice system 100 can modify the affect of the voice of a user during a conversation, according to various embodiments. The voice system 100 may include, without limitation, a microphone 110 and a speaker 120.

As shown, a voice sample 112 is acquired from a user via one or more microphones 110. The voice sample 112 is then processed by modifying one or more acoustic characteristics of the voice sample 112 in order to generate a modified voice sample 114 that more accurately conveys the intended emotion(s). For example, and without limitation, if a user would like to increase the degree of excitement conveyed in his or her voice, then the voice system 100 could process the voice sample 112 to increase the pitch and loudness of the voice sample 112 and/or to modify the prosodic characteristics of the voice sample 112, such as by modifying the pitch, loudness, and/or speech rate or specific words or phrases included in the voice sample 112. By contrast, if a user would like to increase the degree of sadness or sympathy conveyed in his or her voice, then the voice system 100 could process the voice sample 112 to decrease the pitch and speech rate of the voice sample 112 and/or to modify the prosodic characteristics of the voice sample 112 in order to emphasize these particular emotions. The voice system 100 would then output the modified voice sample 114 to a listener via the speaker(s) 120.

In various embodiments, one or more sensors associated with the voice system 100 automatically detect an emotional state of a user. The voice system 100 then modifies a voice sample 112 acquired from the user based on the emotional state in order to enhance, reduce, and/or change the affect of the voice sample 112. For example, and without limitation, if a user has trouble conveying happiness or gratitude, then one or more sensors associated with the voice system 100 could detect verbal and/or non-verbal cues indicating that the user is happy or grateful. The voice system 100 would then modify a voice sample 112 acquired from the user to increase the degree of happiness or gratitude reflected in the voice sample 112, such as by increasing the pitch and/or speech rate of the voice sample 112. Thus, although a person with whom the user is communicating may not understand that certain verbal and/or non-verbal cues portrayed by the user indicate that the user is happy or grateful, the voice system 100 could detect these cues and modify the affect of the voice sample 112 to more effectively convey the happiness or gratitude of the user.

In another non-limiting example, one or more sensors associated with the voice system 100 could detect verbal and/or non-verbal cues indicating that the user is angry or frustrated. The voice system 100 could then modify a voice sample 112 acquired from the user to reduce the degree of anger and/or frustration reflected in the voice sample 112, such as by decreasing the speech rate, lowering the pitch, and/or neutralizing the tone of the voice sample 112. Consequently, in such embodiments, the voice system 100 may enable a user who is feeling angry or frustrated to more politely communicate with others without using an offensive tone of voice. Alternatively, when the voice system 100 detects that the user is angry or frustrated, the voice system 100 could enhance affect in the voice sample 112 to increase the degree of anger and/or frustration reflected in the voice sample 112, such as by adding subharmonic frequencies to the voice sample 112. In such embodiments, the voice system 100 would enable a user who is feeling angry or frustrated, but who is unable to effectively communicate that anger or frustration, to be more accurately understood by others.

Accordingly, in some embodiments, the voice system 100 may enhance the affect of a voice sample 112 when the voice system 100 determines, via one or more sensors, that a user is in a first set of emotional states (e.g., happy, excited, affectionate) and may reduce or change the affect of a voice sample 112 when the user is in a second set of emotional states (e.g., angry, frustrated, sad). Additional techniques for detecting an emotional state of a user via one or more sensors are described below in further detail in conjunction with FIG. 2.

In various embodiments, a user may select one or more emotions that he or she would like to enhance, reduce, and/or change in a voice sample 100. The user may further select the degree to which each emotion should be enhanced, reduced, and/or changed by the voice system 100. In general, a user may choose to enhance, reduce, and/or change the affect in his or her own voice samples 112, or the user may choose to enhance, reduce, and/or change the affect in voice samples 112 acquired from a person with whom the user is communicating. For example, and without limitation, a user could select a first emotion (e.g., "excitement") via a graphical user interface (GUI) associated with the voice system 100 and indicate that this emotion should be enhanced. In response, when the voice system 100 detects that the user and/or a person with whom the user is communicating is excited, the affect of voice samples 112 acquired via the microphone(s) 110 would be modified to emphasize excitement, such as by increasing the loudness, pitch, and/or speech rate of the voice sample 112.

Further, a user could select a second emotion (e.g., "angry") via the GUI associated with the voice system 100 and indicate that this emotion should be reduced. Then, when the voice system 100 detects that the user and/or a person with whom the user is communicating is angry, the affect of voice samples 112 acquired via the microphone(s) 110 would be modified to reduce the anger in the voice sample 112, such as by reducing the speech rate and loudness of the voice sample 112. In yet another non-limiting example, a user could select a third emotion (e.g., "nervous") via the GUI associated with the voice system 100 and indicate that this emotion should be changed. Then, when the voice system 100 detects that the user and/or a person with whom the user is communicating is nervous, the affect of voice samples 112 acquired via the microphone(s) 110 would be changed and replaced with a different emotion, such as confidence.

In some embodiments, the GUI may be implemented on a smartphone or mobile computer display associated with the voice system 100. Additionally, in some embodiments, any of the functionality described herein (e.g., enhance, reduce, change, etc.) may be implemented automatically by the voice system 100, without explicit interaction via a GUI.

Figure 2:
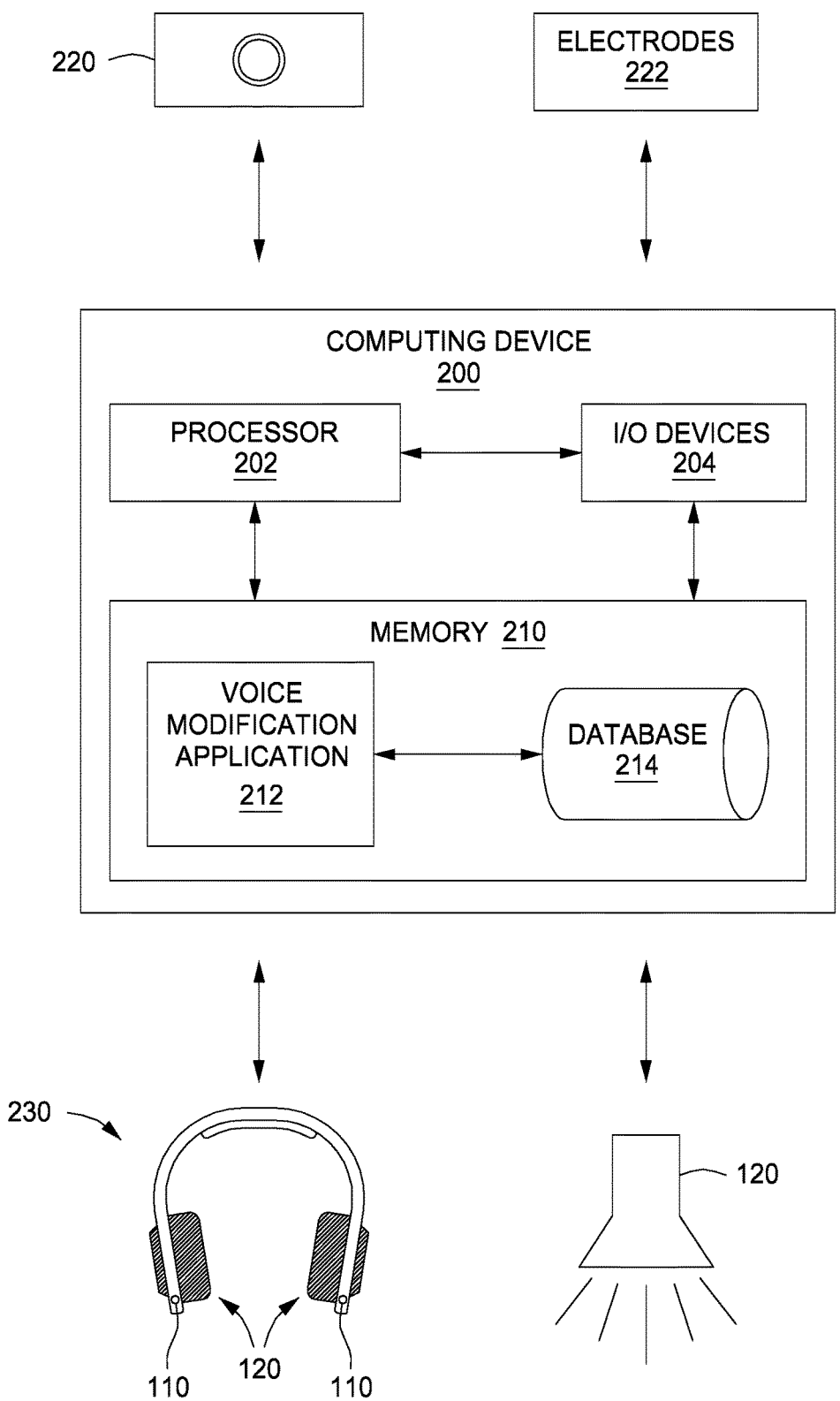
FIG. 2 is an illustration of a computing system configured to implement one or more aspects of the voice affect modification system of FIG. 1, according to various embodiments.

FIG. 2 is an illustration of a computing system configured to implement one or more aspects of the voice system 100 of FIG. 1, according to various embodiments. As shown, the voice system 100 may include, without limitation, one or more microphones 110, one or more speakers 120, a computing device 200, a camera 220, and electrodes 222. The computing device 200 includes a processor 202, input/output (I/O) devices 204, and a memory 210. The memory 210 includes a voice modification application 212 configured to interact with a database 214.

The microphone(s) 110 may include wireless or wired acoustic transducers. For example, and without limitation, the microphone(s) 110 may include single transducers, omnidirectional transducers, directional transducers, and/or microphone arrays that allow dynamic beam forming.

In various embodiments, the voice modification application 212 may determine the emotional state of a user from one or more voice samples 112 acquired via the microphone(s) 110. For example, and without limitation, the voice modification application 212 could detect one or more acoustic characteristics in a voice sample 112 that are indicative of an emotional state. The voice modification application 212 would then modify the acoustic characteristic(s) and/or acoustic characteristics related to other emotional states in real-time to enhance, reduce, or change the affect in the voice sample 112.

In various embodiments, the camera(s) 220 are configured to detect facial expressions of a user, gestures performed by a user, pupil dilation, the posture of a user, and/or the body language of a user. For example, and without limitation, images acquired by the camera(s) 220 may be analyzed to determine the positions and/or appearance of the user's eyes, eyebrows, mouth, nose, forehead, cheeks, fingertips, joints, hands, wrists, arms, shoulders, back, legs, etc. The positions and/or appearance of one of more of these body parts may then be used to determine the emotional state of the user. For example, and without limitation, images of the user's face and/or body may be acquired by the camera(s) 220 and processed by the voice modification application 212 to determine the shape of the eyebrows and mouth of the user and/or the posture of the user. The shape of the eyebrows and mouth of the user and/or the posture of the user may then be analyzed to determine the emotional state of the user. Although only one camera 220 is shown in FIG. 2, any number of cameras 220 located at any positions relative to the user may be used to detect the emotional state of the user and/or the emotional state of a person with whom the user is communicating.

The electrode(s) 222 may include one or more electroencephalography (EEG) electrodes, skin conductance electrodes, heart rate sensor electrodes, and/or electromyography (EMG) electrodes. In general, the electrodes 222 acquire sensor data associated with the emotional state of a user. For example, and without limitation, sensor data acquired via EEG electrodes could be analyzed by the voice modification application 212 to detect brain activity of the user. The voice modification application 212 could then determine the emotional state of the user based on the brain activity and modify one or more voice samples 112 based on that emotional state. Additionally, brain activity indicative of the emotional state of the user may be determined via other types of sensor data, such as sensor data acquired via functional magnetic resonance imaging (fMRI) and functional near-infrared spectroscopy (fNIRS).

In some embodiments, sensor data acquired via skin conductance electrodes and/or heart rate sensor electrodes may be used to determine the emotional state of a user. For example, and without limitation, the voice modification application 212 could process sensor data acquired via one or more skin conductance electrodes to determine that the user is perspiring. Based on this sensor data and optionally in conjunction with other sensor data (e.g., images of the user's face acquired via a camera 220) the voice modification application 212 could then determine that the user is nervous. In another non-limiting example, the voice modification application 212 could process sensor data acquired via a heart rate sensor electrode to determine that the user has an elevated heart rate. Then, based on this sensor data and optionally in conjunction with other sensor data (e.g., spectral analysis of a voice sample 112 of the user), the voice modification application 212 could determine that the user is happy and/or excited.

The voice system 100 may include any number of electrodes 222 configured to be placed in contact with a user's scalp, ear canal, and/or other portions of the user's head or body. In some embodiments, one or more types of electrodes 222 described herein are included in a device that is held or worn by the user, such as in a smartphone, headset, bracelet, armband, chest strap, earbuds, or pair of headphones 230. In still other embodiments, the voice modification application 212 could determine the emotional state of a user by detecting physiological changes in the user via a blood oxygenation sensor, or by detecting movement of the user via an accelerometer, a gyroscope, or a magnetometer.

I/O devices 204 may include input devices, output devices, and devices capable of both receiving input and providing output. For example, and without limitation, I/O devices 204 may include wired and/or wireless communication devices that send data to and/or receive data from the microphone(s) 110, speaker(s) 120, camera 220, and/or electrodes 222 included in the voice system 100. Additionally, the I/O devices 204 may include one or more wired or wireless communication devices that receive other types of sensor data indicative of the emotional state of a user.

In various embodiments, voice system 100 may include a personal audio device, mobile computer, personal digital assistant, mobile phone, desktop computer, or any other device suitable for practicing one or more embodiments described herein. In some embodiments, the voice system 100 includes a pair of headphones 230, such as the over-the-ear headphones shown in FIG. 2, in which one or more microphones 110 are optionally disposed. In general, however, any type of wired or wireless headphones, including circumaural headphones, supra-aural headphones, and in-ear headphones, may be used to perform the techniques described herein. In other embodiments, the voice system 100 may be any acoustic device that is able to capture and reproduce sound for a user, including an assistive medical device, such as a hearing aid, or a mobile communication device, such as a Bluetooth® headset.

Generally, computing device 200 is configured to coordinate the overall operation of the voice system 100. In other embodiments, the computing device 200 may be coupled to, but separate from other components of the voice system 100. In such embodiments, the voice system 100 may include a separate processor that receives voice samples 112 and/or sensor data indicative of the emotional state of a user and transmits data (e.g., sensor data and/or modified voice samples 114) to the computing device 200, which may be included in a separate device, such as a personal computer, wearable device, smartphone, portable media player, etc. However, the embodiments disclosed herein contemplate any technically feasible system configured to implement the functionality of the voice system 100.

Processor 202 may be any technically feasible form of processing device configured process data and execute program code. Processor 202 could be, for example, and without limitation, a central processing unit (CPU), a graphics processing unit (GPU), an application-specific integrated circuit (ASIC), a field-programmable gate array (FPGA), and so forth. Memory 210 may include a memory module or a collection of memory modules. The voice modification application 212 within memory 210 is executed by the processor 202 to implement the overall functionality of the computing device 200 and, thus, to coordinate the operation of the voice system 100 as a whole. For example, and without limitation, voice samples 112 and/or sensor data acquired via the microphone(s) 110, camera 220, and electrodes 222 may be processed by the voice modification application 212 to generate modified voice samples 114 and/or data indicative of the emotional state of a user. In some embodiments, the database 214 stores voice samples 112, modified voice samples 114, audio parameters, sensor data, algorithms, statistics, and user preferences.

In embodiments in which the voice system 100 is implemented in conjunction with headphones 230 or earbuds, the headphones 230 or earbuds may operate in an acoustically transparent mode in which the user can hear ambient sounds in the surrounding environment. In the acoustically transparent mode, the voice modification application 212 could detect voice samples 112 associated with one or more persons with whom the user is communicating (e.g., via selective voice enhancement) and modify the voice samples 112 to enhance, reduce, or change the affect of the voice samples 112. The modified voice samples 114 would then be outputted to the user via speakers 120 included in the headphones 230 or earbuds.

Additionally, the voice system 100 may modify the affect in a voice sample 112 via active noise cancellation techniques, such as by outputting inverted signals via the speakers 120 to cancel specific sound frequencies in the voice sample 112. For example, and without limitation, certain frequencies in the voice of a user could be cancelled via one or more inverted signals in order to enhance, reduce, or change the affect of the voice of the user. Further, the voice system 100 may implement such techniques in conjunction with external speakers 120 (e.g., loudspeakers) that output modified voice samples 114 and/or noise cancellation signals during in-person communications. In such embodiments, the voice modification application 212 could modify a voice sample 112 to enhance, reduce, or change the affect of the voice sample 112 and output the modified voice sample 114 at a similar or louder volume than the user's own voice, allowing the person with which the user is communicating to more accurately perceive the emotional state of the user.

In general, the voice modification application 212 may use any technically feasible algorithms or techniques to modify a voice sample 112 to enhance, reduce, or change the affect associated with the voice sample 112. In some embodiments, the voice modification application 212 modifies acoustic characteristics of voice samples 112 via audio processing techniques such as Fourier transforms, harmonic scaling, pitch scaling, pitch shifting, time stretching, time compression, and resampling. Additionally, commercial technologies, such as Auto-Tune or similar audio processing technologies may be implemented in various embodiments.

Because different users may express emotions differently (e.g., due to cultural or personal reasons), the voice system 100 may include a training mode. In the training mode, the voice system 100 processes sensor data associated with specific emotional states in order to learn the emotional states of the user, enabling the emotional states to be more accurately determined during operation of the voice system 100. In some embodiments, the voice system 100 implements machine learning algorithms in order to generate user heuristics that the voice system 100 can implement to determine emotional states. Such heuristics may then be stored in the database 214 and accessed by the voice modification application 212.

In embodiments in which multiple types of sensor data are acquired by the voice modification application 212 to determine the emotional state of the user, a weighting may be assigned to each type of sensor data. The emotional state(s) of the user may then be determined based on the emotional state determined for each sensor type and the weighting assigned to each of the sensor types. For example, and without limitation, a user could interact with the GUI to assign a first weighting to sensor data associated with brain activity, a second weighting to sensor activity associated with facial expressions, and a third weighting to sensor data associated with acoustic characteristics acquired voice samples 112. The voice modification application 212 would then determine an emotional state indicated by each type of sensor data, apply a weighting to each emotional state, and determine the dominant emotional state based on the weightings. In some embodiments, assigning weightings to specific types of sensor data may enable the voice modification application 212 to more accurately determine the correct emotional state(s) when ambiguous verbal and non-verbal cues are detected. Additionally, assigning weightings to specific types of sensor data may enable the voice modification application 212 to place less emphasis on types of sensor data that may less accurately reflect the emotional state of the user, without completely disregarding these types of sensor data.

FIGS. 3A and 3B illustrate different techniques for generating modified voice samples 114 via the voice system 100 of FIG. 1, according to various embodiments. As shown in FIG. 3A, in some embodiments, a voice modification application 212 executing on the device 310 (e.g., a smartphone) associated with the speaker acquires a voice sample 112, determines the emotional state(s) of the speaker, and transmits both the voice sample 112 and the emotional state(s) to the listener. Then, the device 320 associated with the listener receives the voice sample 112 and the emotional state(s), and a voice modification application 212 executing on the listener device 320 generates a modified voice sample 114 that is outputted to the listener. Thus, in such embodiments, the manner in which the voice sample 112 is processed to enhance, reduce, and/or change affect may be controlled by the listener, such as via a GUI implemented by the voice modification application 212 executing on the listener device 320.

As shown in FIG. 3B, in some embodiments, the voice modification application 212 executing on the device 310 associated with the speaker acquires a voice sample 112, determines the emotional state(s) of the speaker, and modifies the voice sample 112 locally to generate a modified voice sample 114. The modified voice sample 114 is then transmitted to the device 320 associated with the listener and outputted to the listener. Thus, in such embodiments, the manner in which the voice sample 112 is processed to enhance, reduce, and/or change affect may be controlled by the speaker, such as via any of the GUI implementations described above.

Additionally, in the embodiments illustrated in FIGS. 3A and 3B, the speaker and listener may negotiate the degree to which voice samples 112 are modified to enhance, reduce, and/or change affect. In such embodiments, each of the listener and the speaker could select a preferred degree of enhancement, reduction, and/or change for one or more emotional states. The voice modification application 212 may then modify voice samples 112 based on the selections made by the speaker and the listener, such as by selecting the lower degree of enhancement, reduction, and/or change selected by the parties.

Figure 4:
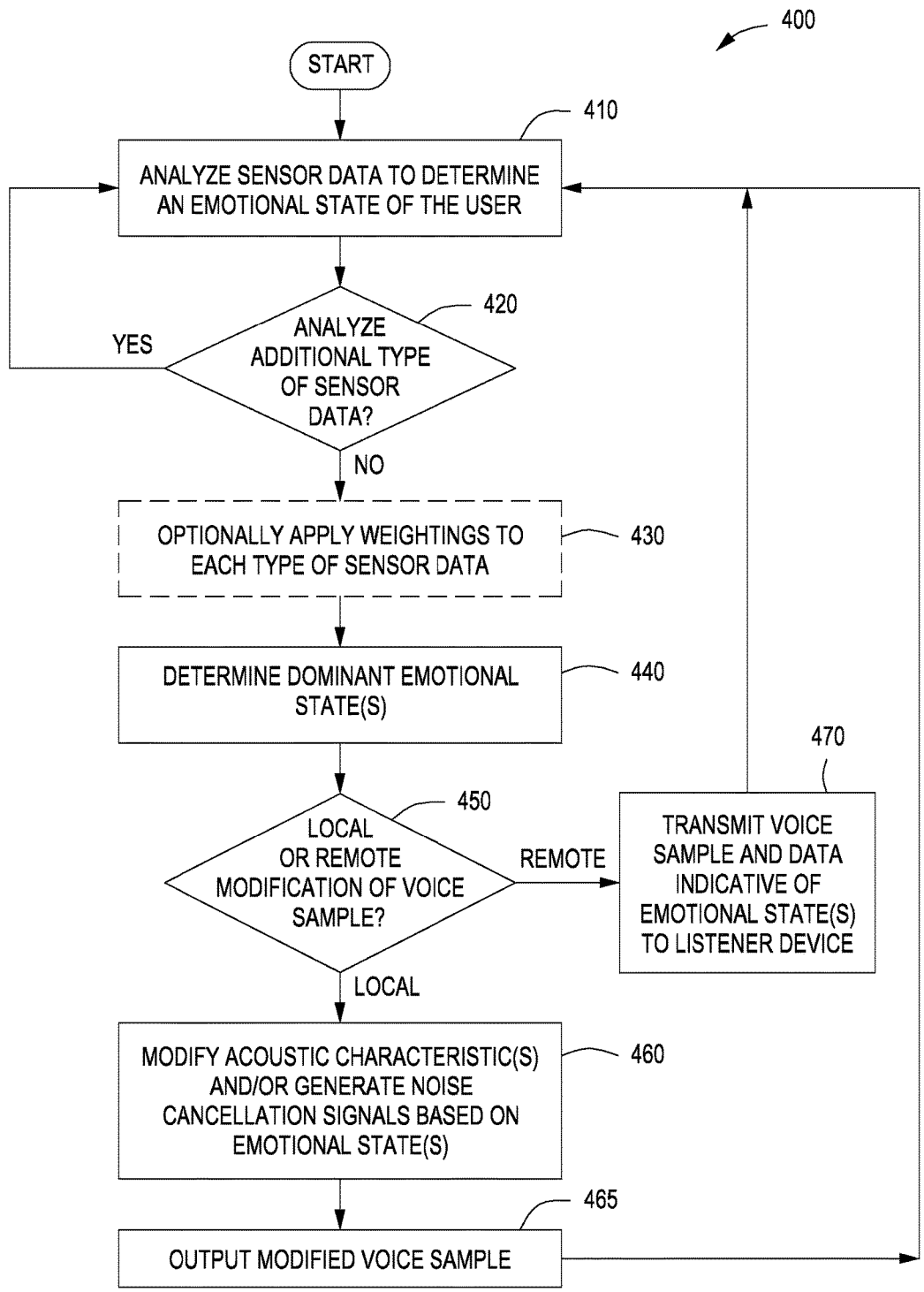
FIG. 4 is a flow diagram of method steps for modifying the affect of a voice, according to various embodiments.

FIG. 4 is a flow diagram of method steps for modifying the affect of a voice, according to various embodiments. Although the method steps are described in conjunction with the systems of FIGS. 1-3B, persons skilled in the art will understand that any system configured to perform the method steps, in any order, falls within the scope of the various embodiments.

As shown, a method 400 begins at step 410, where the voice modification application 212 analyzes sensor data received via the microphone(s) 110, I/O devices 204, camera(s) 220, electrode(s) 222, etc. to determine an emotional state of a user. For example, and without limitation, as described above, the voice modification application 212 could analyze sensor data to detect verbal and/or non-verbal cues indicative of the emotional state of the user. Then, at step 420, the voice modification application 212 determines whether an additional type of sensor data should be analyzed. If an additional type of sensor data should be analyzed, then the method 400 returns to step 410.

If no additional type of sensor data should be analyzed, then the method 400 proceeds to step 430, where the voice modification application 212 optionally applies a weighting to each type of sensor data. As described above, in some embodiments, a user of the voice system 100 may select weightings to apply to each type of sensor data. Additionally, in some embodiments, the voice modification application 212 may automatically apply weightings to one or more types of sensor data.

At step 440, the voice modification application 212 analyzes the emotional state determined for each type of sensor data and determines the dominant emotional state indicated by the sensor data. In embodiments in which weightings are applied to one or more types of sensor data, the voice modification application 212 could determine the dominant emotional state by applying a corresponding weighting to the emotional state determined for each type of sensor data and determining which emotional state has a highest value. For example, and without limitation, the voice modification application 212 could assign a first weighting of 40% to a first type of sensor data (e.g., a voice sample 112 acquired via a microphone 110), a second weighting of 30% to a second type of sensor data (e.g., facial images acquired via a camera 220), and a third weighting of 30% to a third type of sensor data (e.g., brain activity acquired via electrodes 222). Then, if the voice modification application 212 determined a "happy" emotional state for both the first type of sensor data and the second type of sensor data, but determined an "angry" emotional state for the third type of sensor data, then, at step 440, the voice modification application 212 would determine (e.g., based on the total weighting of 70%) that the "happy" emotional state is the dominant emotional state.

In some embodiments, at step 440, the voice modification application 212 could determine multiple dominant emotional states exhibited by the user. For example, and without limitation, the voice modification application 212 could analyze verbal cues (e.g., based on a voice sample 112) to determine a first emotional state and could analyze non-verbal cues (e.g., based on facial expressions) to determine a second emotional state. Then, if the voice modification application 212 determines that the first emotional state does not conflict with the second emotional state, both the first emotional state and the second emotional state could be designated as dominant emotional states. A non-limiting example of conflicting emotional states includes a happy emotional state and a sad emotional state. A non-limiting example of non-conflicting emotional states includes a happy emotional state and a nervous emotional state, or an angry emotional state and a sad emotional state.

Next, at step 450, the voice modification application 212 determines whether voice samples 112 acquired from the user are to be modified locally (e.g., via a speaker device 310) or remotely (e.g., via a listener device 320). If, the voice modification application 212 determines that voice samples 112 are to be modified locally, then the method 400 proceeds to step 460, where the voice modification application 212 modifies one or more acoustic characteristics of the voice sample 112 based on the dominant emotional state(s). Additionally, at step 460, the voice modification application 212 may generate one or more noise cancellation signals based on the dominant emotional state(s) in order to cancel out aspects (e.g., specific frequencies) of the voice sample 112. Then, at step 465, the voice modification application 212 outputs the modified voice sample 114, such as by transmitting the modified voice sample 114 to a listener device 320 and/or by outputting the modified voice sample 114 via a speaker 120. The method 400 then returns to step 410.

Returning to step 450, if the voice modification application 212 determines that voice samples 112 are to be modified remotely, then the method 400 proceeds to step 470, where the voice modification application 212 transmits one or more voice samples 112 and data indicative of the dominant emotional state(s) to a remote device, such as a listener device 320. As described above, transmitting the voice sample(s) 112 and data indicative of the dominant emotional state(s) to a remote device enables a remote user to determine how the voice samples 112 will be processed to enhance, reduce, and/or change the affect in the voice sample(s) 112. The method 400 then returns to step 410.

In sum, the voice modification application determines an emotional state of a user based on one or more types of sensor data. Next, the voice modification application modifies a voice sample acquired from the user in order to enhance, reduce, and/or change the affect of the voice sample based on the emotional state. The voice modification application then outputs the modified voice sample to a listener.

At least one advantage of the techniques described herein is that the affect in the voice of a speaker can be enhanced to enable the speaker to more effectively convey their emotional state and/or to assist a listener in more effectively determining the emotional state of the speaker. In addition, the affect in the voice of a speaker can be reduced and/or changed, for example, and without limitation, to mask an emotional state of the speaker. Moreover, the emotional state of a speaker may be automatically determined via one or more types of sensor data, without requiring interaction from the speaker or listener.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable processors or gate arrays.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. A non-transitory computer-readable storage medium including instructions that, when executed by a processor, configure the processor to modify an affect of a voice, by performing the steps of:
    determining that a first emotional state and a second emotional state associated with a person are not in conflict with each other;
    classifying each of the first emotional state and the second emotional state as dominant emotional states;
    in response to classifying each of the first emotional state and the second emotional state as dominant emotional states, modifying one or more acoustic characteristics of a voice sample acquired from the person based on the first emotional state and the second emotional state to alter an affect associated with the voice sample;
    generating a second voice sample based on the one or more acoustic characteristics that have been modified; and
    transmitting the second voice sample.

2. The non-transitory computer-readable storage medium of claim 1, wherein determining that the first emotional state and the second emotional state associated with the person are not in conflict with each other comprises analyzing visual sensor data to determine one or more facial characteristics of the person.

3. The non-transitory computer-readable storage medium of claim 1, wherein determining that the first emotional state and the second emotional state associated with the person are not in conflict with each other comprises analyzing the voice sample to detect at least one acoustic characteristic reflective of the emotional state.

4. The non-transitory computer-readable storage medium of claim 3, wherein the at least one acoustic characteristic includes at least one of a pitch, a vocal perturbation, a loudness, and a speech rate.

5. The non-transitory computer-readable storage medium of claim 1, wherein determining that the first emotional state and the second emotional state associated with the person are not in conflict with each other comprises analyzing brain activity of the person.

6. The non-transitory computer-readable storage medium of claim 1, wherein modifying the one or more acoustic characteristics of the voice sample comprises at least one of increasing a pitch associated with the voice sample or decreasing the pitch associated with the voice sample.

7. The non-transitory computer-readable storage medium of claim 1, wherein modifying the one or more acoustic characteristics of the voice sample comprises at least one of increasing a speed associated with the voice sample, decreasing the speed associated with the voice sample, increasing a loudness associated with the voice sample, or decreasing the loudness associated with the voice sample.

8. The non-transitory computer-readable storage medium of claim 1, wherein determining that the first emotional state and the second emotional state are not in conflict with each other comprises:
    analyzing a first type of sensor data associated with the person to determine a first emotional state;
    assigning a first weighting to the first emotional state;
    analyzing a second type of sensor data associated with the person to determine a second emotional state;
    assigning a second weighting to the second emotional state;

analyzing a third type of sensor data associated with the person to determine a third emotional state; and assigning a third weighting to the third emotional state, wherein the emotional state is based on the first emotional state, the second emotional state, the third emotional state, the first weighting, the second weighting, and the third weighting.

9. The non-transitory computer-readable storage medium of claim 1, wherein determining that the first emotional state and the second emotional state associated with the person are not in conflict with each other comprises receiving a selection of the emotional state via a graphical user interface.

10. A system for modifying an affect of a voice, the system comprising:

a microphone configured to acquire a voice sample from the user;

one or more sensors configured to acquire sensor data associated with the user;

a memory storing a voice modification application; and a processor coupled to the microphone, the one or more sensors, and the memory, wherein, when executed by the processor, the voice modification application configures the processor to:

determine that a first emotional state and a second emotional state associated with a person are not in conflict with each other based on the sensor data;

classify the first emotional state and the second emotional state as a first dominant emotional state and a second dominant emotional state, respectively;

in response to classifying the first emotional state and the second emotional state as the first dominant emotional state and the second dominant emotional state, respectively, modify one or more acoustic characteristics of the voice sample based on at least one of the first dominant emotional state and the second dominant emotional state to alter an affect associated with the voice sample;

generate a second voice sample based on the one or more acoustic characteristics that have been modified; and transmit the second voice sample.

11. The system of claim 10, wherein the processor is configured to determine that the first emotional state and the second emotional state associated with the person are not in conflict with each other by analyzing the voice sample to detect at least one acoustic characteristic associated with at least one of the first emotional state and the second emotional state.

12. The system of claim 10, wherein the one or more sensors comprise a camera, and the processor is configured to determine that the first emotional state and the second emotional state associated with the person are not in conflict with each other by analyzing one or more images acquired via the camera to determine one or more facial characteristics of the person.

13. The system of claim 10, wherein the one or more sensors comprise a camera, and the processor is configured to determine that the first emotional state and the second emotional state associated with the person are not in conflict with each other by analyzing one or more images acquired via the camera to determine at least one of a gesture performed by the person and a body posture of the person.

14. The system of claim 10, wherein the sensor data comprises signals indicative of brain activity of the person, and the processor is configured to determine that the first emotional state and the second emotional state associated with the person are not in conflict with each other based on the brain activity.

15. The system of claim 14, wherein the signals indicative of brain activity of the user comprise at least one of electroencephalogram (EEG) signals, functional magnetic resonance imaging (fMRI) signals, and functional near-infrared spectroscopy (fNIRS) signals.

16. The system of claim 10, wherein the second voice sample comprises a noise cancellation signal, and wherein, when executed by the processor, the voice modification application configures the processor to transmit the second voice sample by outputting the noise cancellation signal via a speaker to modify a voice of the person.

17. A method for modifying an affect of a voice, the method comprising:

acquiring sensor data associated with a person and a voice sample from the person;

determining that a first emotional state and a second emotional state associated with the person are not in conflict with each other based on the sensor data;

classifying each of the first emotional state and the second emotional state as dominant emotional states; and in response to classifying each of the first emotional state and the second emotional state as dominant emotional states, transmitting the voice sample and data indicative of at least one of the first emotional state and the second emotional state to a remote device.

18. The method of claim 17, wherein the sensor data comprises at least one of an acoustic characteristic of the voice of the person, a facial expression of the person, and brain activity of the person.

19. The method of claim 17, wherein the remote device is configured to modify the voice sample based on the at least one of the first emotional state and the second emotional state associated with the person to generate a second voice sample, and output the second voice sample.

* * * * *